(12) United States Patent
Rambo et al.

(10) Patent No.: US 9,255,916 B2
(45) Date of Patent: Feb. 9, 2016

(54) GAS DETECTION MANAGEMENT SYSTEM WITH REPLACEMENT MODULES

(71) Applicant: Honeywell International Inc., Morristown, NJ (US)

(72) Inventors: Tan Rambo, Canmore (CA); Clive Warden Kennard, Calgary (CA)

(73) Assignee: Honeywell International Inc., Morris Plains, NJ (US)

( * ) Notice: Subject to any disclaimer, the term of this patent is extended or adjusted under 35 U.S.C. 154(b) by 505 days.

(21) Appl. No.: 13/689,356

(22) Filed: Nov. 29, 2012

(65) Prior Publication Data

US 2014/0144204 A1    May 29, 2014

(51) Int. Cl.
*G01N 33/00* (2006.01)

(52) U.S. Cl.
CPC .................................. *G01N 33/0006* (2013.01)

(58) Field of Classification Search
None
See application file for complete search history.

(56) References Cited

U.S. PATENT DOCUMENTS 6,244,093 B1*  6/2001  Parekh ........................ 73/1.06
2006/0156789 A1*  7/2006  Frank et al. ................. 73/1.06

* cited by examiner

*Primary Examiner* — Robert R Raevis
(74) *Attorney, Agent, or Firm* — Conley Rose, P.C.; Kristin Jordan Harkins

(57) ABSTRACT

A calibration system is provided that supports a plurality of multi-gas detectors and that includes additional options for delivering additional test gases to the detectors. The system can include a calibration module for calibrating a multi-gas detector with a first gas and a replacement module capable of being coupled to the calibration module. When coupled to the calibration module, the replacement module can support delivering a plurality of test gases, not including the first test gas, to the calibration module.

18 Claims, 6 Drawing Sheets

GAS DETECTION MANAGEMENT SYSTEM WITH REPLACEMENT MODULES

FIELD

The present invention relates generally to gas detection management systems. More particularly, the present invention relates to a gas detection management system with replacement modules.

BACKGROUND

Many known calibration systems include a single test gas inlet to calibrate a plurality of single gas detectors. For example, FIG. 1 is a system block diagram of a calibration system 100 that includes a single test gas inlet to calibrate a plurality of single gas detectors. As seen in FIG. 1, the calibration system 100 can include a master module 110 and a plurality of test modules 120-1, 120-2, 120-3, 120-4. Although only four test modules are shown in FIG. 1, the calibration system 100 can support any number of test modules as would be known by those of skill in the art, for example, ten test modules.

In the calibration system 100, each of the master module 110 and the test modules 120-1, 120-2, 120-3, 120-4 can include a solenoid 130, 130-1, 130-2, 130-3, 130-4, respectively, therein. Purge gas 140 and quad gas 150 can enter the master module 110 via respective gas inlets and be processed by the solenoid 130 before passing through each of the test modules 120-1, 120-2, 120-3, 120-4 and their respective solenoids 130-1, 130-2, 130-3, 130-4 in sequence. Accordingly, test module 120-4 can receive the purge gas 140 or the quad gas 150 only after each of the test modules 120-1, 120-2, and 120-3 receive the purge gas 140 or the quad gas 150.

The calibration system 100 may be suitable for calibrating a plurality of single gas detectors for a single gas. However, many users of calibration systems are requiring the ability to calibrate a plurality of single gas detectors for a plurality of different gases. For example, FIG. 2 is a system block diagram of a calibration system 200 that includes a plurality of test gas inlets to calibrate a plurality of single gas detectors. As seen in FIG. 2, the master module 210 can include two solenoids 230, 230' therein, while each of the test modules 210-1, 210-2, 210-3, 210-4 can include one solenoid 230-1, 230-2, 230-3, 230-4, respectively therein. Quad gas 250 can enter the master module 210 via a respective test gas inlet and be processed by the first solenoid 230 and exotic 1 gas 260 can enter the master module 210 via a respective test gas inlet and be processed by the second solenoid 230' before passing through each of the test modules 210-1, 210-2, 210-3, 210-4 and their respective solenoids 230-1, 230-2, 230-3, 230-4 in sequence.

Although only two solenoids 230, 230' in the master module 210 are shown in FIG. 2, the master module 210 can include any number of solenoids as would be known by those of skill in the art, for example, five solenoids. The master module 210 can support a plurality of test gas inlets, but must include a respective solenoid therein for each supported test gas inlet. Accordingly, the master module 210 of the calibration system 200 in FIG. 2 must be factory configured for the number of test gas inlets supported. Thus, depending on a user's needs, he may have to purchase a new master module to support additional test gas inlets.

While the calibration systems 100, 200 may be suitable for calibrating a plurality of single gas detectors, many users of calibration systems are also requiring the ability to calibrate a plurality of multi-gas detectors. For example, FIG. 3 is a system block diagram of a calibration system 300 for calibrating a plurality of multi-gas detectors. As seen in FIG. 3, the calibration system 300 need not include a master module and, instead, includes a plurality of test modules, 320-1, 320-2, 320-3, 320-4.

The calibration system 300 includes four gas inlets corresponding to purge gas 340, quad gas 350, exotic 2 gas 360, and exotic 1 gas 370, respectively. The calibration system 300 also includes lines 310-1, 310-2, 310-3, 310-4, for example, tubing or piping, corresponding to the purge gas 340, quad gas 350, exotic 2 gas 360, and the exotic 1 gas 370, respectively. The lines 310-1, 310-2, 310-3, 310-4 are configured so that each line 310-1, 310-2, 310-3, 310-4, flows through each test module 320-1, 320-2, 320-3, 320-4 regardless of whether the gas 340, 350, 360, 370 corresponding to the line 310-1, 310-2, 310-3, 310-4 is actually delivered to and/or processed by the test module 320-1, 320-2, 320-3, 320-4. This configuration allows gas to be delivered to downstream, out-of-sequence modules without first having to be sequentially delivered to upstream modules. This configuration also allows for simultaneous and independent calibration of the test modules.

For example, as seen in FIG. 3, line 310-1 corresponding to purge gas 340 can flow through each test module 320-1, 320-2, 320-3, 320-4 and be processed by each test module 320-1, 320-2, 320-3, 320-4 via a respective solenoid 330-1, 330-2, 330-3, 330-4 therein. Line 310-2 corresponding to quad gas 350 can also flow through each test module 320-1, 320-2, 320-3, 320-4 and be processed by each test module 320-1, 320-2, 320-3, 320-4 via the respective solenoid 330-1, 330-2, 330-3, 330-4 therein. However, line 310-3 corresponding to exotic 2 gas 360 can flow through each test module 320-1, 320-2, 320-3, 320-4, but only be delivered to test module 320-3, 320-4 and processed by solenoids 330-3', 330-4' therein. Similarly, line 310-4 corresponding to exotic 1 gas 370 can flow through each test module 320-1, 320-2, 320-3, 320-4, but only be delivered to test modules 320-2, 320-4 and processed by respective solenoids 330-2', 330-4" therein.

As seen in FIG. 3 and described above, each test module 320-1, 320-2, 320-3, 320-4 includes a number of solenoids therein corresponding to the number of gases delivered thereto and processed thereby, not including the purge gas. Accordingly, each test module 320-1, 320-2, 320-3, 320-4 must be factory configured for the number of test gases supported. Thus, depending on a user's needs, he may have to purchase new test modules to support additional solenoids and test gases delivered to the module.

For example, only the purge gas 340 and the quad gas 350 are delivered to test module 320-1. Accordingly, the test module 320-1 includes one solenoid 330-1. The purge gas 340, the quad gas 350, and the exotic 1 gas 370 are delivered to test module 320-2. Accordingly, the test module 320-2 includes two solenoids 330-2, 330-2'. Similarly, the purge gas 340, the quad gas 350, and the exotic 2 gas 360 are delivered to test module 320-3. Accordingly, the test module 320-3 also includes two solenoids 330-3, 330-3'. The purge gas 340, the quad gas 350, the exotic 2 gas 360, and the exotic 1 gas 370 are all delivered to test module 320-4. Accordingly, the test module 320-4 includes three solenoids 330-4, 330-4', 330-4".

In view of the above, there is a continuing, ongoing need for a calibration system that supports a plurality of multi-gas detectors, but that also includes additional options for supporting additional test gases delivered to the detectors.

DETAILED DESCRIPTION

Figure 1:
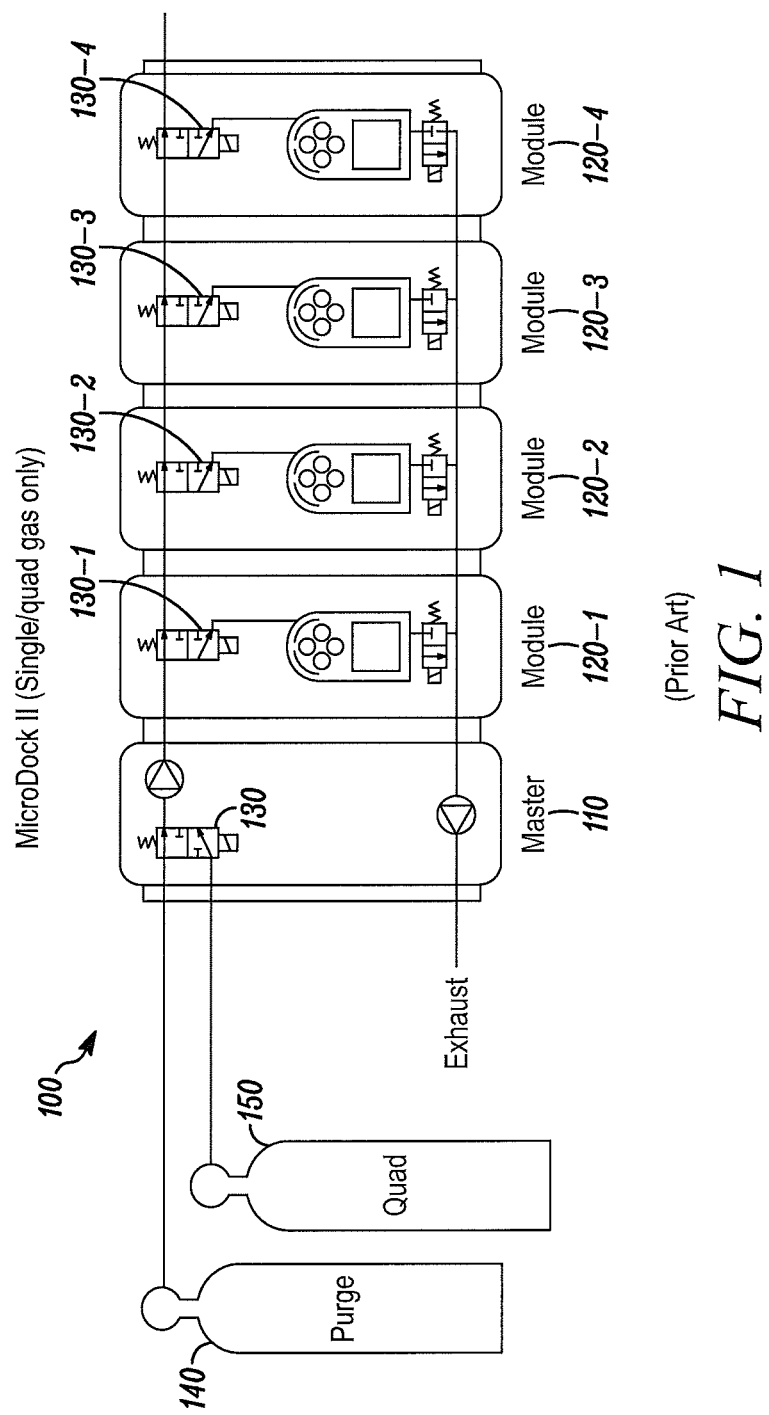
FIG. 1 is a system block diagram of a calibration system that includes a single test gas inlet to calibrate a plurality of single gas detectors as known in the art.
Figure 2:
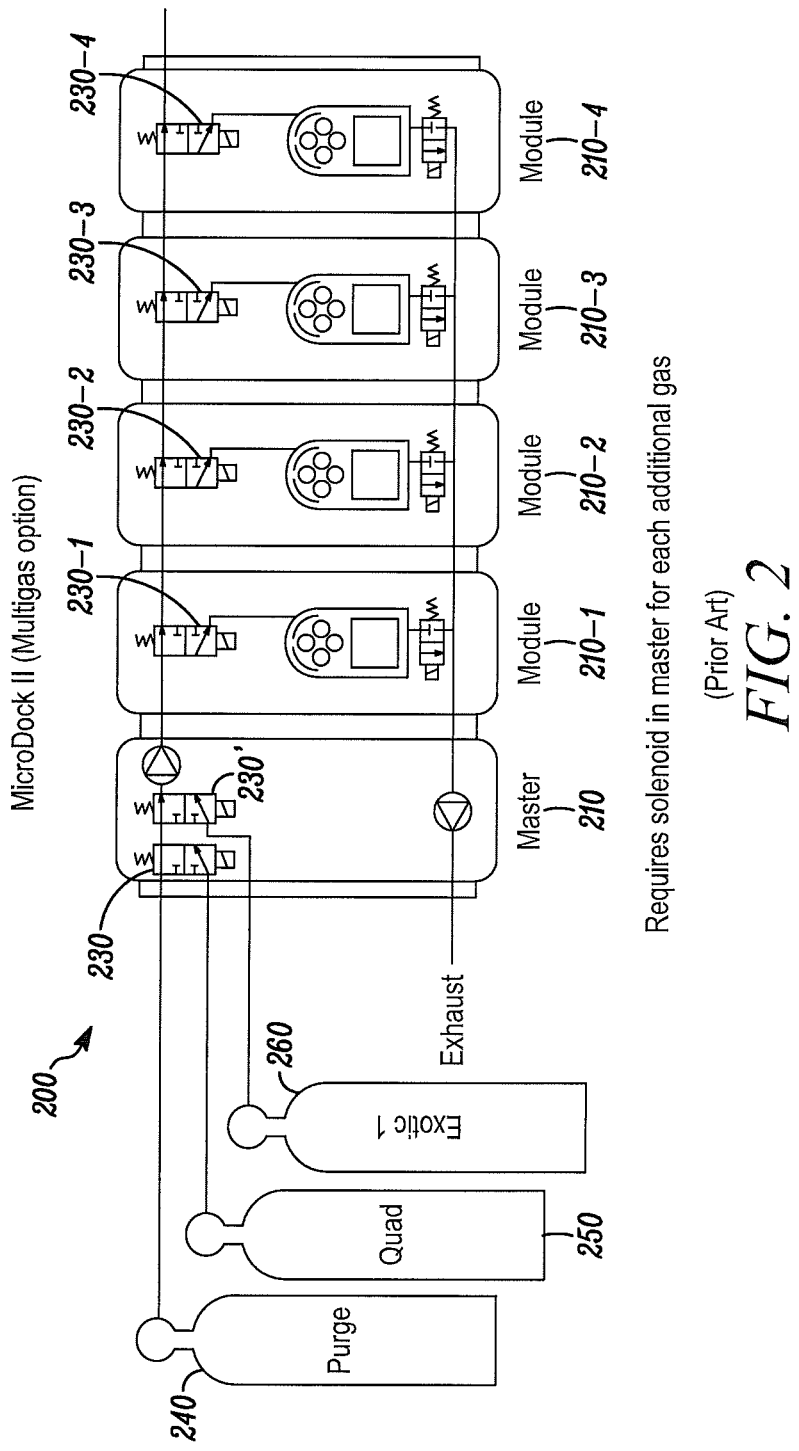
FIG. 2 is a system block diagram of a calibration system that includes a plurality of test gas inlets to calibrate a plurality of single gas detectors as known in the art.
Figure 3:
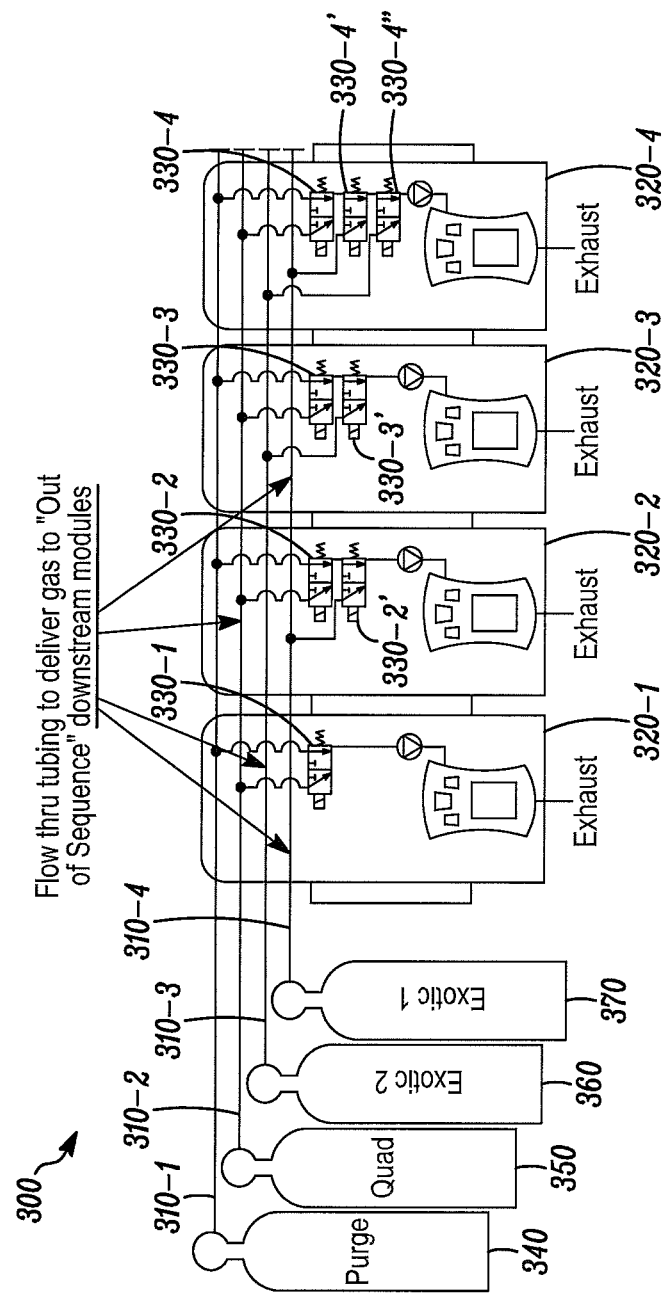
FIG. 3 is a system block diagram of a calibration system for calibrating a plurality of multi-gas detectors as known in the art.

While this invention is susceptible of an embodiment in many different forms, there are shown in the drawings and will be described herein in detail specific embodiments thereof with the understanding that the present disclosure is to be considered as an exemplification of the principles of the invention. It is not intended to limit the invention to the specific illustrated embodiments.

Embodiments disclosed herein include a calibration system that supports a plurality of multi-gas detectors and that includes additional options for supporting additional test gases delivered to the detectors. For example, some embodiments of the system disclosed herein can include a gas expansion module that can be installed into a calibration module and that can enable additional test gases to be delivered to the calibration module.

The calibration system disclosed herein can allow each calibration module in the system to perform substantially simultaneous and independent calibration. For example, a single gas expansion module can be installed in a single calibration module in the system so as not to interfere with a neighboring module's ability to perform its own calibration.

In some embodiments, a calibration module can have a standard configuration that includes a bypass module. Parallel gas plumbing lines that correspond to the additional test gases in the calibration system can flow through each calibration module in the system. However, a bypass module can prevent the parallel gas plumbing lines from delivering the additional test gases to a respective calibration module for processing.

The bypass module can be plugged into a main body of a calibration module in the system. However, the bypass module can also be unplugged from the main body of a calibration module. When unplugged from the main body of the calibration module, the bypass module can be replaced by the expansion module. For example, the expansion module can be plugged into the main body of the calibration module. Accordingly, the main body of the calibration module can be an outlet for either the bypass module or the expansion module.

Unlike the bypass module, the expansion module can facilitate the parallel gas plumbing lines delivering the additional test gases to a respective calibration module. For example, the expansion module can include plumbing lines that connect to respective ones of the parallel gas plumbing lines in such a way so as to deliver a test gas from the parallel gas plumbing lines to a respective solenoid in the expansion module.

Figure 4:
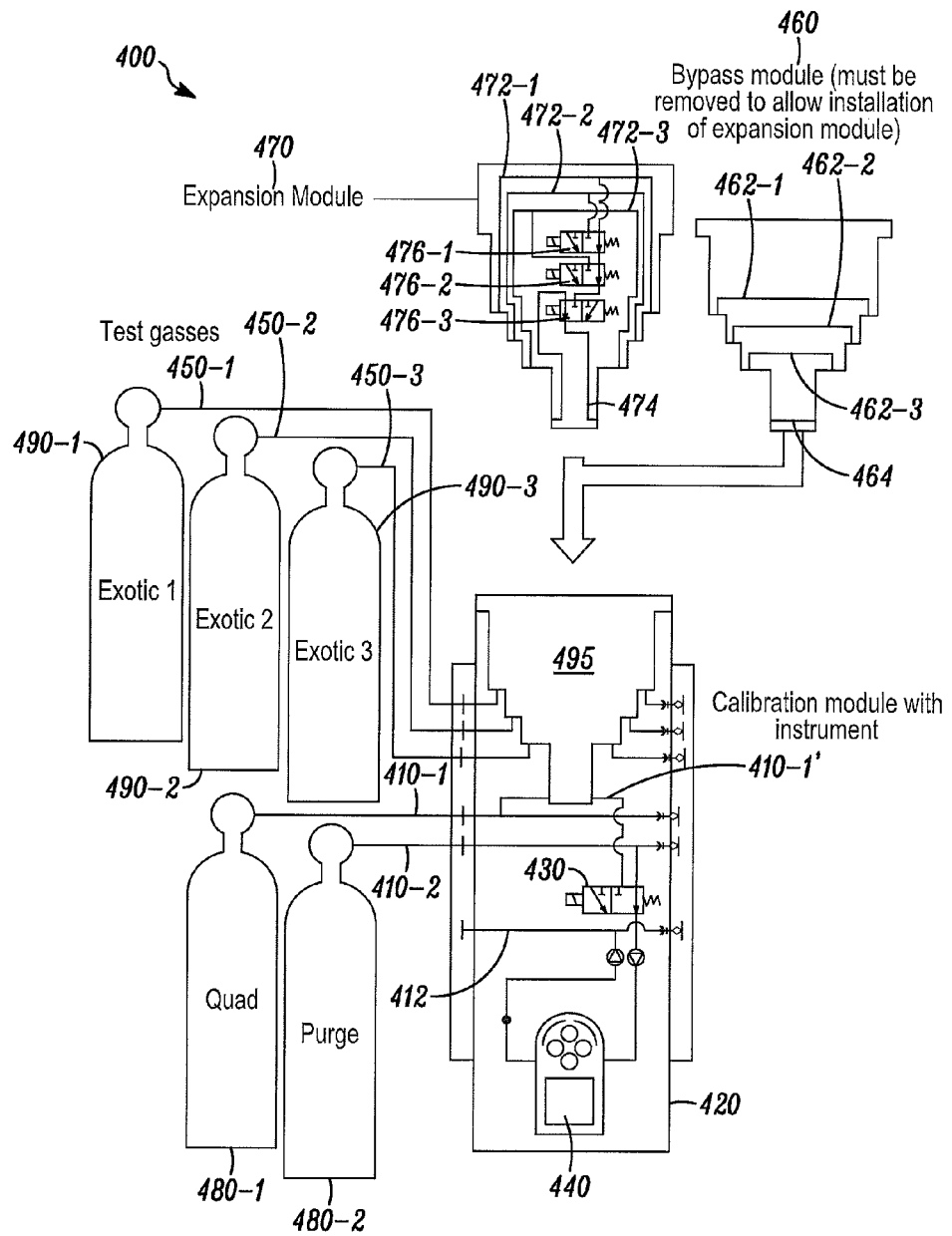
FIG. 4 is a system block diagram of a calibration system for plugging a bypass module or an expansion module into a single calibration module in accordance with disclosed embodiments.

FIG. 4 is a system block diagram of a calibration system 400 for plugging a bypass module 460 or an expansion module 470 into a single calibration module 420 in accordance with disclosed embodiments. The calibration system 400 in accordance with disclosed embodiments need not include a master module. However, as seen in FIG. 4, the main body of a calibration module 420 in the system 400 can support a solenoid 430, a detector under test 440, first and second plumbing lines 410-1, 410-2, and a plurality of test gas lines 450-1, 450-2, 450-3.

The first plumbing line 410-1 can flow through the main body of the calibration module 420 and deliver the quad gas 480-1 to the solenoid 430 via a first gas inlet. Similarly, the second plumbing line 410-2 can flow through the main body of the calibration module 420 and deliver the purge gas 480-2 to the solenoid 430 via a second gas inlet.

Each of the plurality of test gas lines 450-1, 450-2, 450-3 can correspond to respective ones of test gases, for example, exotic 1 gas 490-1, exotic 2 gas 490-2, and exotic 3 gas 490-3, respectively. However, as seen in FIG. 4, the plurality of test gas lines 450-1, 450-2, 450-3 do not deliver the test gases 490-1, 490-2, 490-3 to the solenoid 430. Instead, each of the plurality of test gas lines 450-1, 450-2, 450-3 can enter the main body of the calibration module 420 via a respective gas inlet and exit the main body of the calibration module via a respective gas outlet. In between the gas inlet and outlet, each of the plurality of test gas lines 450-1, 450-2, 450-3 need not be continuous. Instead, each of the plurality of test gas lines 450-1, 450-2, 450-3 can terminate at first and second ends of an outlet 495 of the main body of the calibration module 420.

Either a bypass module 460 or an expansion module 470 can be inserted or plugged into the outlet 495 of the main body of the calibration module 420. In a standard configuration, the bypass module 460 can be plugged into the main body of the calibration module 420, and the calibration module 420 can support one test gas, for example, the quad gas 480-1, as well as the purge gas 480-2. However, in an expanded configuration, the expansion module 470 can be plugged into the main body of the calibration module 420, and the calibration module 420 can support four test gases, for example, the quad gas 480-1, exotic 1 gas 490-1, exotic 2 gas 490-2, and exotic 3 gas 490-3, as well as the purge gas 480-2.

Figure 5:
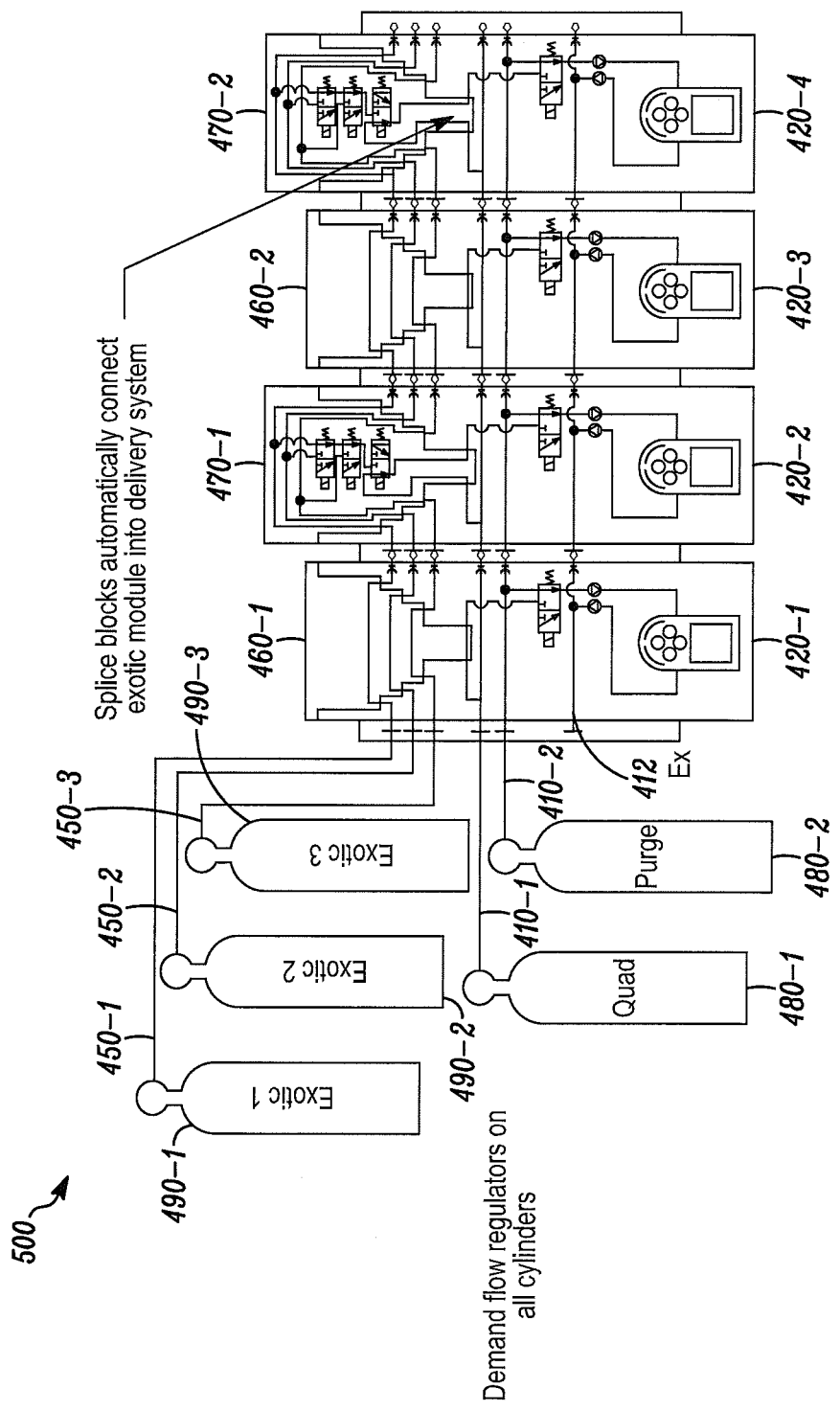
FIG. 5 is a system block diagram of a calibration system that includes a bypass module plugged into each of a first plurality of calibration modules and that includes an expansion module plugged into each of a second plurality of calibration modules in accordance with disclosed embodiments.

As seen in FIG. 4, the bypass module 460 can include a plurality of bypass gas lines 462-1, 462-2, 462-3 as well as a delivery line 464. Each of the plurality of bypass gas lines 462-1, 462-2, 462-3 can correspond to a respective one of the plurality of test gas lines 450-1, 450-2, 450-3 in the main body of the calibration module 420. Accordingly, as seen in FIG. 5, when the bypass module 460 is plugged into the main body of a calibration module 420, each of the bypass lines 462-1, 462-2, 462-3 can connect with or be coupled to a respective one of the plurality of test gas lines 450-1, 450-2, 450-3 at first and second ends of the outlet 495 to form one continuous line for passing a respective test gas 490-1, 490-2, 490-3 through the main body of the calibration module 420, via the bypass module 460.

The delivery line 464 can correspond to a spliced line 410-1' in the main body of the calibration module 420. For example, the spliced line 410-1' can be an offshoot line of the first plumbing line 410-1. As seen in FIG. 5, when the bypass module 460 is plugged into the main body of the calibration module 420, the delivery line 464 can tap into the spliced line 410-1' to connect the bypass module 460 to the delivery system of the main body of the calibration module 420.

As seen in FIG. 4, the expansion module 470 can include a plurality of gas expansion lines 472-1, 472-2, 472-3, a plurality of solenoids 476-1, 476-2, 476-3, and a delivery line 474. Each of the plurality of gas expansion lines 472-1, 472-2, 472-3 can correspond to a respective one of the plurality of test gas lines 450-1, 450-2, 450-3 in the main body of the calibration module 420. Accordingly, as seen in FIG. 5, when the expansion module 470 is plugged into the main body of the calibration module 420, each of the gas expansion lines 472-1, 472-2, 472-3 can connect with or be coupled to respective ones of the plurality of test gas lines 450-1, 450-2, 450-3 at first and second ends of the outlet 495 to form one continuous line for passing a respective test gas 490-1, 490-2, 490-3 through the main body of the calibration module 420, via the expansion module 470.

The expansion module 470 can also include a plurality of solenoids 476-1, 476-2, 476-3 therein, and the number of solenoids in the plurality can correspond to the number of test gases delivered thereto. For example, the calibration system 400 seen in FIG. 4 includes three test gases 490-1, 490-2, 490-3. Accordingly, the expansion module 470 includes three solenoids 476-1, 476-2, 476-3, each solenoid corresponding to a respective one of the test gases 490-1, 490-2, 490-3.

The delivery line 474 can correspond to the spliced line 410-1' in the main body of the calibration module 420. As seen in FIG. 5, when the expansion module 470 is plugged into the main body of a calibration module 420, the delivery line 474 can tap into the spliced line 410-1' to connect the expansion module 470 to the delivery system of the main body of the calibration module 420.

FIG. 5 is a system block diagram of a calibration system 500 that includes a plurality of calibration modules 420-1, 420-2, 420-3, 420-4. Although only four calibration modules are shown in FIG. 5, the calibration system 500 in accordance with disclosed embodiments can support any number of calibration modules as would be known by those of skill in the art.

A bypass module 460 can be plugged into each of a first plurality of calibration modules 420, and an expansion module 470 can be plugged into each of a second plurality of calibration modules 420. As seen in FIG. 5, the first plurality of calibration modules can include calibration modules 420-1, 420-3. However, it is to be understood that the first plurality could include all, none, or any number of the calibration modules 420. Similarly, as seen in FIG. 5, the second plurality of calibration modules can include calibration modules 420-2, 420-4. However, it is to be understood that the second plurality could also include all, none, or any number of the calibration modules 420-1, 420-2, 420-3, 420-4.

That is, an expansion module 470 can be plugged into any calibration module 420-1, 420-2, 420-3, 420-4 in the system 500 as would be desired by a user. Regardless of which and how many expansion modules 470 are used, each of the test gases 490-1, 490-2, 490-3 can be delivered to calibration modules 420 connected to an expansion module 470 and be prevented from being delivered to calibration modules 420 without an expansion module 470, that is, calibration modules 420 connected to a bypass module 460. In this manner, calibration modules 420 connected to respective expansion modules 470 can perform simultaneous and independent calibration for any of the test gases 490.

Figure 6:
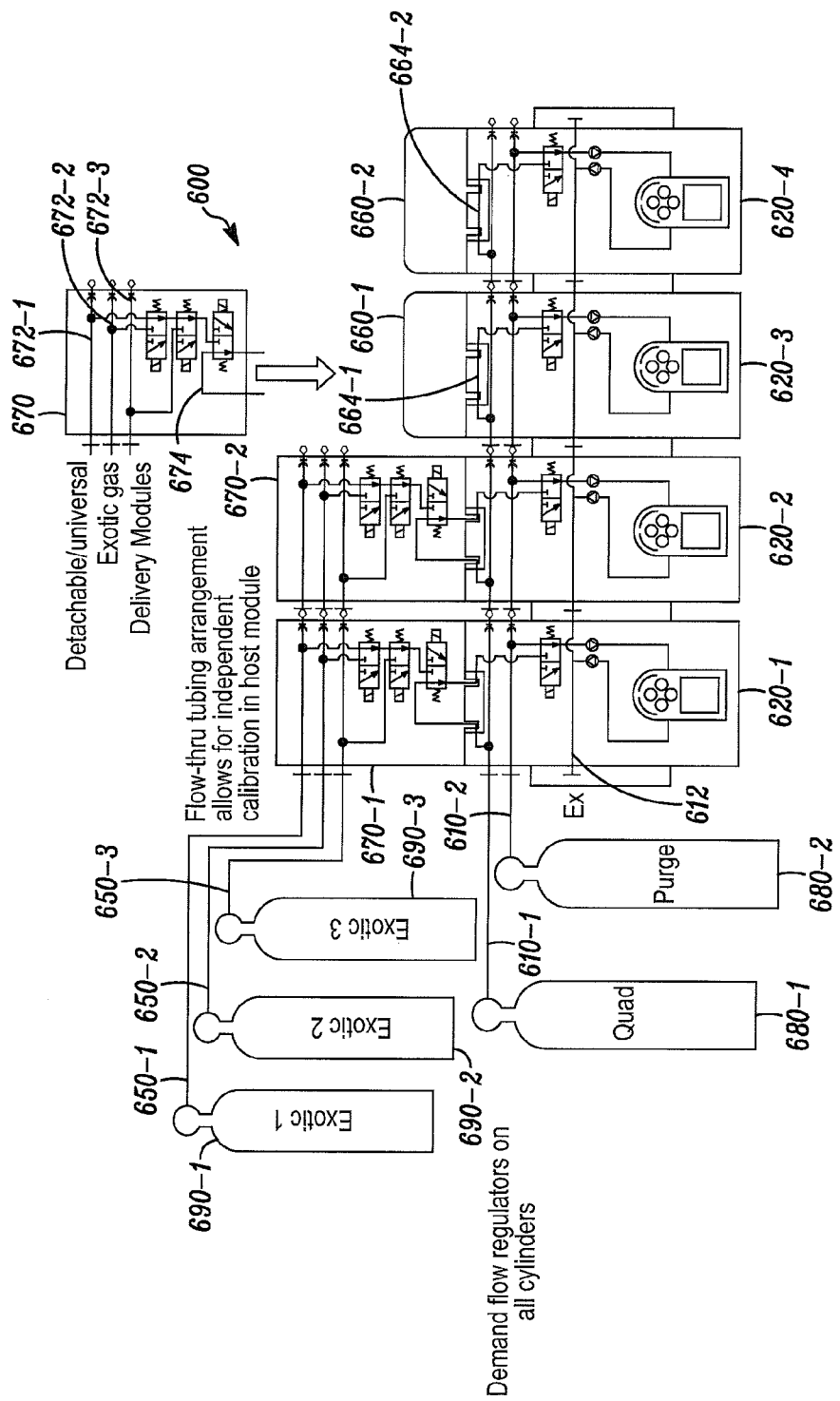
FIG. 6 is a system block diagram of a calibration system that includes a bypass module plugged into each of a first plurality of calibration modules and that includes an expansion module plugged into each of a second plurality of calibration modules in accordance with alternate disclosed embodiments.

FIG. 6 is a system block diagram of a calibration system 600 in accordance with an alternate disclosed embodiment. The calibration system 600 includes a plurality of calibration modules 620-1, 620-2, 620-3, 620-4. Although only four calibration modules are shown in FIG. 6, the calibration system 600 can support any number of calibration modules as would be known by those of skill in the art.

The main body of the calibration module 620 in FIG. 6 is similar to the calibration modules 420 as seen in FIGS. 4 and 5. However, the main body of the calibration module 620 includes only two gas inlets and two gas outlets—one inlet and outlet each for the quad gas 680-1 and for the purge gas 680-2. As seen in FIG. 6, the main body of the calibration module 620 does not include a gas inlet or a gas outlet for the test gases 690-1, 690-2, 690-3. Instead, the expansion module 670 shown in FIG. 6 can include a plurality of test gas inlets and a plurality of test gas outlets connected by respective ones of a plurality of gas expansion lines 672-1, 672-2, 672-3. Each test gas inlet and each test gas outlet can correspond to a respective one of the test gases 690-1, 690-2, 690-3. Accordingly, in the embodiment shown in FIG. 6, no portion of the test gas lines 650-1, 650-2, 650-3 is supported by the main body of the calibration module 620.

Because the main body of the calibration module 620 does not support the test gas lines 650-1, 650-2, 650-3, the bypass module 660 need not include bypass lines. Accordingly, as seen in FIG. 6, the bypass module 660 does not include any bypass lines and, instead, only includes a delivery line 664 for connecting to or coupling to the delivery system in the main body of the calibration module 620.

Although the system 600 as seen in FIG. 6 includes expansion modules 670-1, 670-2 plugged into calibration modules 620-1, 620-2 and bypass modules 660-1, 660-2 plugged into calibration modules 620-3 and 620-4, it is to be understood that embodiments disclosed herein are not so limited. Instead, an expansion module 670 could be plugged into all, none, or any number of the calibration modules 620-1, 620-2, 620-3, 620-4. Similarly, a bypass module 660 could be plugged into all, none, or any number of the calibration modules 620-1, 620-2, 620-3, 620-4. For example, a bypass module 660 could be plugged into calibration modules 620-1, 620-2, and an expansion module 670 could be plugged into calibration modules 620-3, 620-4. In accordance with disclosed embodiments, test gases 690-1, 690-2, 690-3 can be delivered only to a calibration module 620 that is plugged into an expansion module 670.

As seen in FIGS. 4-6, the systems 400, 500, and 600 can also include an exhaust line 412, 612. In embodiments disclosed herein, exhaust can be pumped through the exhaust line 412, 612 to ensure correct flow rates over the sensors of the detector under test. In some embodiments, the exhaust can be pumped in one calibration module regardless of what the other calibration modules in the system are doing.

Although a few embodiments have been described in detail above, other modifications are possible. For example, the logic flows described above do not require the particular order described, or sequential order, to achieve desirable results. Other steps may be provided, or steps may be eliminated, from the described flows, and other components may be added to, or removed from, the described systems. Other embodiments may be within the scope of the invention.

From the foregoing, it will be observed that numerous variations and modifications may be effected without departing from the spirit and scope of the invention. It is to be understood that no limitation with respect to the specific system or method described herein is intended or should be inferred. It is, of course, intended to cover all such modifications as fall within the sprit and scope of the invention.

What is claimed is:

1. A system comprising:
   at least one calibration module for calibrating a multi-gas detector; and an expansion module capable of being inserted into an outlet of the calibration module, wherein the calibration module includes:
- a first solenoid,
- a main delivery line coupled to the first solenoid,
- a plurality of test gas inlets coupled to respective ones of a first plurality of test gas lines terminating at a first side of the outlet, and
- a plurality of test gas outlets coupled to respective ones of a second plurality of test gas lines terminating at a second side of the outlet, wherein the expansion module includes:
- a plurality of solenoids coupled to each other,
- an expansion delivery line coupled to one of the plurality of solenoids, and
- a plurality of gas expansion lines coupled to respective ones of the plurality of solenoids, wherein, when the expansion module is inserted into the outlet of the calibration module, the expansion delivery line couples to the main delivery line, and wherein, when the expansion module is inserted into the outlet of the calibration module, the plurality of gas expansion lines couples to respective ones of the first plurality of test gas lines and to respective ones of the second plurality of test gas lines so that gas in each of the first plurality of test gas lines flows to a respective one of the plurality of solenoids, via a respective one of the plurality of gas expansion lines.

2. The system of claim 1 further comprising a bypass module capable of being inserted into the outlet of the calibration module, wherein the bypass module includes:
- a bypass delivery line, and
- a plurality of gas bypass lines, wherein, when the bypass module is inserted into the outlet of the calibration module, the bypass delivery line couples to the main delivery line, and wherein, when the bypass module is inserted into the outlet of the calibration module, the plurality of gas bypass lines couples to respective ones of the first plurality of test gas lines and to respective ones of the second plurality of test gas lines so that gas in each of the first plurality of test gas lines flows to a respective one of the second plurality of test gas lines, via a respective one of the plurality of gas bypass lines.

3. The system of claim 1 wherein the calibration module includes a purge gas inlet and a purge gas outlet, the purge gas inlet continuously coupled to the purge gas outlet by a purge gas line.

4. The system of claim 3 wherein the purge gas line is coupled to the first solenoid and to the multi-gas detector.

5. The system of claim 1 wherein the calibration module includes a delivery gas inlet and a delivery gas outlet, the delivery gas inlet continuously coupled to the delivery gas outlet by the main delivery line.

6. The system of claim 5 wherein a first portion of the main delivery line terminates at the first side of the outlet, and wherein a second portion of the main delivery line terminates at the second side of the outlet.

7. The system of claim 1 wherein a number of solenoids in the plurality of solenoids is equal to a number of gas expansion lines in the plurality of gas expansion lines.

8. The system of claim 1 wherein the plurality of test gas inlets are coupled to respective ones of a plurality of test gas tanks.

9. The system of claim 1 wherein the calibration module includes an exhaust gas inlet and an exhaust gas outlet, the exhaust gas inlet continuously coupled to the exhaust gas outlet by an exhaust line.

10. A system comprising:
- at least one calibration module for calibrating a multi-gas detector; and
- an expansion module capable of being inserted into an outlet of the calibration module, wherein the calibration module includes:
- a first solenoid, and
- a main delivery line coupled to the first solenoid, wherein the expansion module includes:
- a plurality of solenoids coupled to each other,
- an expansion delivery line coupled to one of the plurality of solenoids,
- a plurality of test gas inlets coupled to respective ones of a plurality of gas expansion lines, and
- a plurality of test gas outlets coupled to respective ones of the plurality of gas expansion lines, the plurality of gas expansion lines coupled to respective ones of the plurality of solenoids, wherein, when the expansion module is inserted into the outlet of the calibration module, the expansion delivery line couples to the main delivery line.

11. The system of claim 10 further comprising a bypass module capable of being inserted into the outlet of the calibration module, wherein the bypass module includes a bypass delivery line, and wherein, when the bypass module is inserted into the outlet of the calibration module, the bypass delivery line couples to the main delivery line.

12. The system of claim 10 wherein the calibration module includes a purge gas inlet and a purge gas outlet, the purge gas inlet continuously coupled to the purge gas outlet by a purge gas line.

13. The system of claim 12 wherein the purge gas line is coupled to the first solenoid and to the multi-gas detector.

14. The system of claim 10 wherein the calibration module includes a delivery gas inlet and a delivery gas outlet, the delivery gas inlet continuously coupled to the delivery gas outlet by the main delivery line.

15. The system of claim 14 wherein a first portion of the main delivery line terminates at a first side of the outlet, and wherein a second portion of the main delivery line terminates at a second side of the outlet.

16. The system of claim 10 wherein a number of solenoids in the plurality of solenoids is equal to a number of gas expansion lines in the plurality of gas expansion lines.

17. The system of claim 10 wherein the plurality of test gas inlets are coupled to respective ones of a plurality of test gas tanks.

18. The system of claim 10 wherein the calibration module includes an exhaust gas inlet and an exhaust gas outlet, the exhaust gas inlet continuously coupled to the exhaust gas outlet by an exhaust line.

* * * * *